(12) United States Patent
Boime

(10) Patent No.: US 6,689,365 B1
(45) Date of Patent: Feb. 10, 2004

(54) SINGLE-CHAIN FERTILITY HORMONES WITH FSH AND LH ACTIVITY

(75) Inventor: Irving Boime, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/565,930

(22) Filed: May 5, 2000

Related U.S. Application Data

(63) Continuation-in-part of application No. 09/558,033, filed on Apr. 25, 2000, now abandoned.

(51) Int. Cl.⁷ ............................................. C12N 15/16
(52) U.S. Cl. ................ 424/192.1; 435/69.7; 435/69.4; 435/325; 435/320.1; 435/360; 435/365.1; 424/198.1; 530/398; 530/397; 530/412; 530/402
(58) Field of Search ...................... 435/69.4; 424/192.1, 424/198.1

(56) References Cited

U.S. PATENT DOCUMENTS 5,792,460 A * 8/1998 Boime ..................... 424/192.1
6,103,501 A * 8/2000 Boime et al. .............. 435/69.7

FOREIGN PATENT DOCUMENTS

| WO | WO90/09800 | 9/1990 |
|---|---|---|
| WO | WO91/16922 | 11/1991 |
| WO | WO94/24148 | 10/1994 |
| WO | WO95/22340 | 8/1995 |
| WO | WO96/05224 | 2/1996 |
| WO | WO99/25849 | 5/1999 |
| WO | WO00/23473 | 4/2000 |

OTHER PUBLICATIONS

Garcia–Campayo, V. et al. (2001) *Endocrinology* 12(142):5203–5211.
Trout, S.W. et al (1999) *Fertility & Sterility* 72(6):1093–1099.
Fares, F.A., et al., *Proc Natl Acad Sci USA* (1992) 89:4304–4308.
LaPolt, P.S., et al., *Endocrinology* (1992) 131:2514–2520.
Lapthorn, A.J., et al., *Nature* (1994) 369:455–461.
Masatoshi Kanda, et al., *Molecular Endocrinology* (1999) 13:1873–188.
Patel, D.J., *Nature* (1994) 369:438–439.
Wu, H., et al., *Structure* (1994) 2:545–558.

\* cited by examiner

*Primary Examiner*—Lorraine Spector
*Assistant Examiner*—Dong Jiang
(74) *Attorney, Agent, or Firm*—Morrison & Foerster LLP

(57) ABSTRACT

Glycosylated or nonglycosylated proteins of the formula

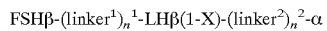

wherein FSHβ is a vertebrate follicle stimulating hormone β subunit or a variant thereof;

LHβ(1-X) refer's to a β subunit of a vertebrate luteinizing hormone containing positions 1-X where X is an integer of 114–121 or a variant thereof;

each "linker" is a hydrophilic, flexible amino acid sequence containing 1-100 amino acid residues;

each n is a 0 or 1; and

α is the α subunit of a vertebrate glycoprotein hormone or a variant thereof are useful in protocols to enhance fertility in humans and in animals.

16 Claims, 6 Drawing Sheets

SINGLE-CHAIN FERTILITY HORMONES WITH FSH AND LH ACTIVITY

This is a CIP of U.S. application Ser. No. 09/558,033, filed Apr. 25, 2000, now abandoned.

TECHNICAL FIELD

The invention relates to a specific class of single-chain fertility hormones. The single-chain forms contain two β subunits upstream of the a subunit. The hormones of the invention have similar activities with respect to follicle stimulating hormone (FSH) function, but differing activities with respect to luteinizing hormone (LH) function. Thus, the compounds of the invention have variable ratios of FSH and LH activity.

BACKGROUND ART

In humans, four important glycoprotein hormone heterodimers (LH, FSH, thyroid stimulating hormone (TSH) and chorionic gonadotropin CG) have identical α subunits and differing β subunits. Three of these hormones are present in virtually all other vertebrate species as well; CG has so far been found only in primates and in the placenta and urine of pregnant mares. FSH is an important hormone in regulating fertility; FSH has been used both in vivo and in vitro to enhance fertility. LH also appears to play a role in such treatments.

Two published PCT applications describe single chain forms of the four hormones FSH, LH, TSH and CG wherein the α and β unit are covalently linked to result in a fusion peptide of the general formulas:

$$\beta(\text{linker})_n\alpha \text{ or}$$

$$\alpha(\text{linker})_n\beta$$

wherein n is 0 or 1 and α and β represent the respective subunits of these hormones: Moyle, W. R., PCT application WO95/22340 published Aug. 24, 1995 and the application of the inventor herein, WO96/05224 published Feb. 22, 1996. The disclosure of these documents is incorporated herein by reference.

Forms of the above-described single-chain glycoprotein hormones in which the number of cystine bridges has been depleted are disclosed in U.S. Ser. No. 08/933,693 filed Sep. 19, 1997, and incorporated herein by reference.

PCT application published as WO99/25849, published May 27, 1999, discloses additional single-chain forms which contain two β subunits linked to a single α subunit. These proteins are of the formula:

$$\beta^1 (\text{linker}^1)_m\text{-}\beta^2\text{-}(\text{linker}^2)_n\text{-}\alpha;$$

$$\alpha\text{-}(\text{linker}^1))_m\text{-}\beta^1\text{-}(\text{linker}^1))_n\text{-}B^2 \text{ and}$$

$$\beta^1\text{-}(\text{linker}^1))_m\text{-}\alpha\text{-}\beta^2\text{-}(\text{linker}^2))_n.$$

This genus includes a large number of individual members and the publication does not focus on any particular subclass. The contents of this document are incorporated herein by reference.

In addition, PCT application PCT/US 99/23555 filed Oct. 12, 1999 and also incorporated herein by reference, discloses additional forms of the hormones which contain two β subunits, but wherein one of the β subunits is bound non-covalently to a single-chain form containing a single β and an α subunit.

Of additional relevance to present invention are publications wherein the carboxy terminal peptide (CTP) of human chorionic gonadotropin or a variant thereof is used to modify pharmaceuticals in general, and these hormones in particular. Thus, PCT application publication number WO90/09800, published Sep. 7, 1990, and incorporated herein by reference, describes various modified forms of these hormones, including C-terminal extension of the β subunit by CTP or a variant. Other muteins of these hormones are also described. "CTP" is the sequence of amino acids extending from any one of positions 112–118 to position 145 of the β subunit of human chorionic gonadotropin. In addition, PCT application publication number WO94/24148 published Oct. 27, 1994, incorporated herein by reference, describes modifying these hormones and other compounds by extension or insertion of the CTP at locations other than the C-terminus and with CTP fragments shorter than the sequence extending from positions 112–118 to 145.

The CTP-extended β subunit of FSH is also described in two papers by applicants herein: LaPolt, P. S., et al., *Endocriniology* (1992) 131:2514–2520 and Fares, F. A., et al., *Proc Natl Acad Sci USA* (1992) 89:4304–4308. Both of these papers are incorporated herein by reference. Also incorporated by reference is an article by the inventors herein which describes the activity of a single-chain compound:. FSHβ-CG β-α: Masatoshi Kanda, et al., *Molecular Endocrinology* (1999) 13: 1873–1881.

The crystal structure of the heterodimeric form of human chorionic gonadotropin has now been published in more or less contemporaneous articles; one by Lapthom, A. J., et al., *Nature* (1994) 369:455–461 and the other by Wu, H., et al., *Structure* (1994) 2:545–558. The results of these articles are summarized by Patel, D. J., *Nature* (1994) 369:438–439.

PCT application WO91/16922 published Nov. 14, 1991 describes a multiplicity of chimeric and otherwise modified forms of the heterodimeric glycoprotein hormones. In general, the disclosure is focused on chimeras of α subunits or β subunits involving portions of various α or β chains respectively. One construct simply listed in WO91/16922, and not otherwise described, fuses substantially all of the β chain of human chorionic gonadotropin to the α subunit preprotein, i.e., including the secretory signal sequence for this subunit.

It has now been found that a particular subset of the genus of biofunctional single-chain compounds disclosed in the above referenced PCT publication WO99/25849 have particularly advantageous properties when used in protocols for enhanced fertility in vitro and in vivo. In this subset, FSH activity is maintained at a level comparable to that of the native hormone, but LH activity is varied over a range generally lower than that of native LH.

DISCLOSURE OF THE INVENTION

The invention provides single-chain forms of fertility inducing hormones that have varying ratios of LH activity as compared to FSH activity. In general, the, single-chain forms have FSH agonist activity comparable to the activity exhibited by equivalent amount of native FSH, but have LH agonist activity which is variable among the various embodiments of the class. Generally, the compounds have LH agonist activities in varying degrees, but typically less than that associated with the native hormone. The single-chain forms of the invention may either be glycosylated, partially glycosylated, or nonglycosylated and the FSHβ is linked through a linker to LHβ. The α subunit is downstream from both.

Thus, in one aspect, the invention is directed to a glycosylated or nonglycosylated protein of the formula $$\text{FSH}\beta\text{-}(\text{linker}^1)_n^1\text{-}\text{LH}\beta(1\text{-}X)\text{-}(\text{linker}^2)_n^2\text{-}\alpha$$

wherein "α" designates the common α subunit of the glycoprotein hormones or a variant thereof; FSHβ refers to the β subunit of follicle stimulating hormone; LHβ(1-X) refers to the luteinizing hormone β subunit optionally containing deletion of up to seven amino acids from said carboxy terminus; each "linker" is an amino acid sequence which is flexible and hydrophilic and may be CTP. CTP refers to the carboxy terminal peptide of chorionic gonadotropin β subunit as further defined hereinbelow. Each n is 0 or 1. However, in one set of preferred embodiments, if both n=1 and both linkers=CTP, X cannot be 114 or if linker$^1$ is CTP, LHβ(1-X)-(linker$^2$)- cannot be replaced by CGβ.

In other aspects, the invention is directed to recombinant materials and methods to produce the proteins of the invention, to pharmaceutical compositions containing them; to antibodies specific for them; and to methods for their use.

MODES OF CARRYING OUT THE INVENTION

Figure 1:
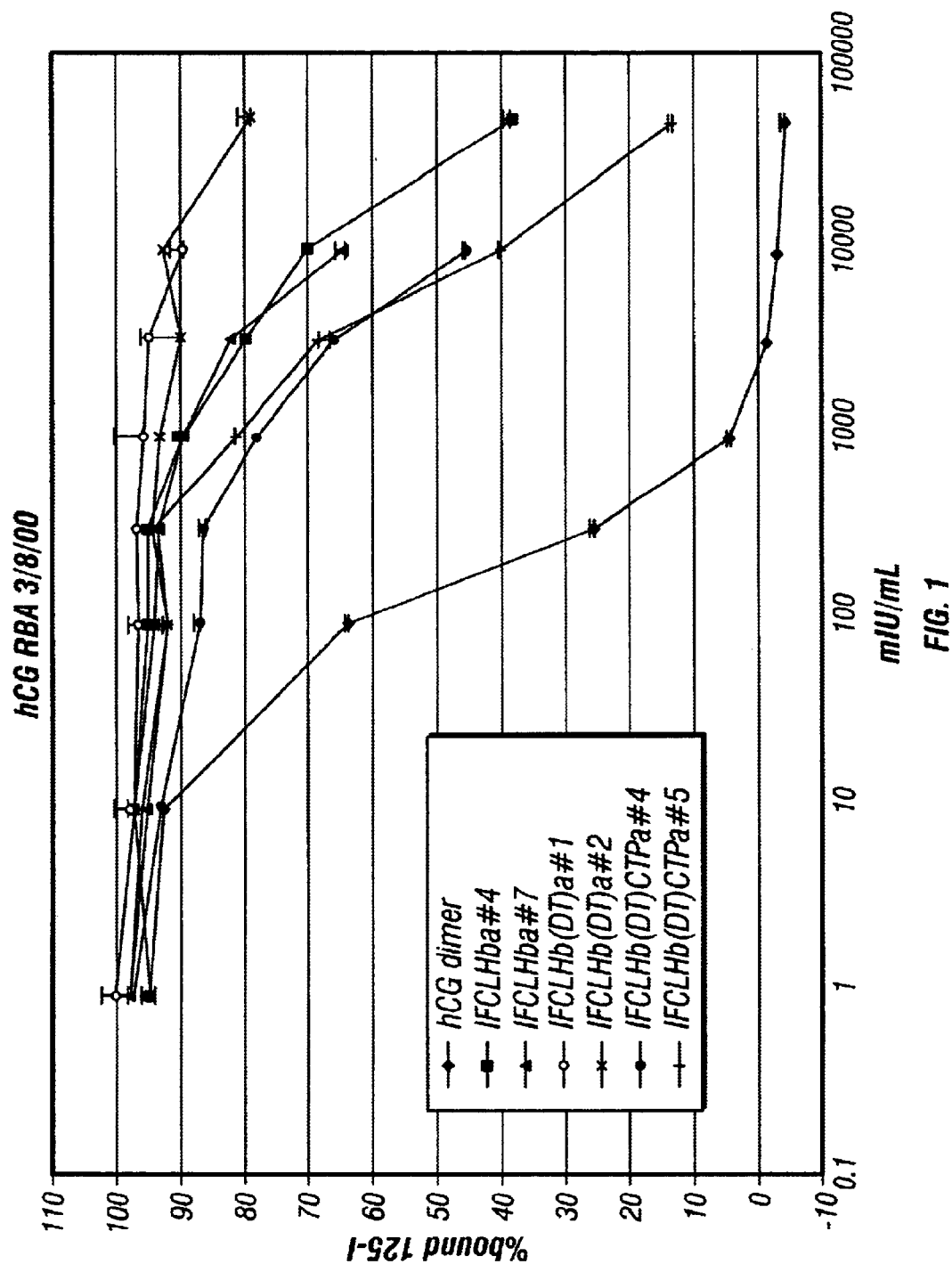
FIG. 1 shows the binding of various compounds of the invention to the LH receptor in competition with labeled hCG.

Four "glycoprotein" hormones in humans provide a family which includes human chorionic gonadotropin (hCG), follicle stimulating hormone (FSH), luteinizing hormone (LH), and thyroid stimulating hormone (TSH). All of these hormones are heterodimers comprised of α subunits which, for a given species, are identical in amino acid sequence among the group, and β subunits which differ according to each member of the family. Thus, normally these glycoprotein hormones occur as heterodimers composed of α and β subunits that are non-covalently associated. Most vertebrates produce FSH, TSH and LH; chorionic gonadotropin has been found only in primates, including humans, and in pregnant mares.

In animals, the α and β subunit of each hormone are encoded by different genes and are synthesized separately and then assembled into the noncovalent heterodimeric complex. In the compounds of the invention the β subunits are covalently linked to an α subunit into a single-chain molecule which is essentially linear in primary structure. The three dimensional structure conferred by secondary and tertiary structural considerations and energy of conformation is apparently sufficiently similar to the heterodimeric form to permit the functionality of the heterodimer represented by the β subunits to be exhibited. The general properties of the genus of compounds which contain, in a single-chain, an α subunit and two β subunits, are described in the above cited PCT application publication WO99/25849. However, the compounds of the present invention, which form a very small subset of those described in the above cited PCT application, are particularly advantageous in the design of pharmaceuticals for inducing fertility.

In treating cells either in in vitro or in vivo for induction of fertility, it is desirable to provide the effects of follicle stimulating hormone (FSH) as the major component. However, it is advantageous to provide a typically lesser, but nevertheless significant amount of activity with respect for receptors for chorionic gonadotropin/luteinizing hormone. (The same receptor recognizes both CG and LH). The degree of LH activity that is desirable varies somewhat with the particular subject or cells to be treated, but it is typically substantially less than that of the FSH activity. The compounds of the present invention provide a group of biologically active molecules which share substantially the same agonistic activity as FSH but provide a range of LH activity ranging, typically, from, an activity of about 1% of the FSH agonist stimulation to about 100% of the FSH agonist stimulation. This range is generated by manipulating the LHβ component with respect to its level of glycosylation, with respect to the inclusion (or not) of a linker and linker, length, and with respect to C terminal deletions as is further described below.

The Subunit Components

As used herein, the common α subunit, and FSH, LH, and CG β subunits as well as the heterodimeric forms have their conventional definitions and refer to the proteins having the amino acid sequences known in the art per se, or allelic variants thereof, regardless of the glycosylation pattern exhibited or other derivatization of the amino acid side chains.

"Native" forms of these peptides are those which have the amino acid sequences that have been isolated from the relevant vertebrate tissue, and have these known sequences perse, or those of their allelic variants. Included in this definition are the C-terminal truncations of the LH β subunit amounting to 7 or less amino acid deletions.

"Variant" forms of the subunits in the proteins and of CTP units (see below) are those which have deliberate alterations, including truncations, in amino acid sequences of the native protein produced by, for example, site-specific mutagenesis or by other recombinant manipulations, or which are prepared synthetically.

These alterations consist of 1–5, preferably 1–3, and more preferably 1 amino acid changes, including deletions,:and/or insertions, and/or substitutions, including in addition to non-conservative substitutions, conservative amino acid substitutions. The resulting variants must retain an activity that reflects that the native hormone—i. e., they must retain the biological activity of the native hormone so as to behave as agonists. However, as set forth below, additional specified substitutions in LHβ(1-X) are permitted.

"Conservative analog" means, in the conventional sense, an analog wherein the residue substituted is of the same general amino acid category as that for which substitution is made. Amino acids have been classified into such groups, as is understood in the art, by, for example, Dayhoff, M., et al., *Atlas of Protein Sequences and Structure* (1972) 5:89–99. In general, acidic amino acids fall into one group; basic amino acids into another; neutral hydrophilic amino acids into another; and so forth. More specific classifications are set forth in WO 96/05224 incorporated by reference above.

One set of preferred variants is that wherein the glycosylation sites of either the α or β subunits or both or of the CTP or partial CTP have been altered. Some useful variants of the hormone quartet described herein are set forth in U.S. Pat. No. 5,177,193 issued Jan. 5, 1993 and incorporated herein by reference. The glycosylation patterns can be altered by destroying the relevant sites, by adding one or more sites, or, in the alternative, by changing the host cell in which the protein is produced.

Variants also include those with noncritical regions altered or removed. Such deletions and alterations may comprise entire loops, so that sequences of considerably more than 10 amino acids may be deleted or changed. The resulting variants must, however, retain at least the receptor binding domains and the regions involved in signal transduction.

There is considerable literature on variants of the glycoprotein hormones and it is clear that a large number of possible variants which result in agonist activity can be prepared. Such variants are disclosed, for example, in Chen, F., et al., *Molec Endocrinol* (1992):6:914–919; Yoo, J., et al., *J Biol Chem* (1993) 268:13034–13042; Yoo, J., et al., *J Biol Chem* (1991) 266:17741–17743; Puett, D., et al., Glycoprotein Hormones, Lusbader, J. W., et al., EDS, Springer Verlag New York (1994) 122–134; Kuetmann, H. T., et al., (ibid) pages 103–117; Erickson, L. D., et al., Endocrinology (1990) 126:2555–2560; and Bielinska, M., et al., *J Cell Biol* (1990) 111:330*a* (Abstract 1844).

Other variants include those wherein one or more cystine-bonds are deleted, typically by substituting a neutral amino acid for one or both cysteines which participate in the link. Particularly preferred cystine bonds which may be deleted are those between positions 26 and 110 and between positions 23 and 72.

As used herein "peptide" and "protein" are used interchangeably, since the length distinction between them is arbitrary.

"Noncritical" regions of the α and β subunits are those regions of the molecules not required for biological activity. In general, these regions are distant from binding sites, precursor cleavage sites, and catalytic regions. Regions critical for inducing proper folding, binding to receptors, catalytic activity and the like should be evaluated. It should be noted that some of the regions which are critical in the case of the dimer become noncritical in single chain forms since the conformational restriction imposed by the molecule may obviate the necessity for these regions. The ascertainment of noncritical regions is readily accomplished by deleting or modifying candidate regions and conducting an appropriate assay for the desired activity. Regions where modifications result in loss of activity are critical; regions wherein the alteration results in the same or similar activity are considered noncritical.

As used herein, the "CTP unit" refers to an amino acid sequence found at the carboxy terminus of human chorionic gonadoropin β subunit which extends from amino acid. 112–118 to residue 145 at the C-terminus. Thus, each "complete" CTP unit contains 28–34 amino acids, depending on the N-terminus of the CTP.

By a "partial" CTP unit is meant an amino acid sequence which occurs between positions 112–118 to 145 inclusive, but which has at least one amino acid deleted from the shortest possible "complete" CTP unit (i.e., from positions 118–145). These "partial" sequences are included in the definition of "variants" with respect to CTP. The "partial" CTP units contain at least one O-glycosylationsite. The CTP unit contains four glycosylation sites at the serine residues at positions 121 (site 1); 127 (site 2); 132 (site 3); and 138 (site 4). The partial forms of CTP useful in agonists will contain one or more of these sites arranged in the order in which they appear in the native CTP sequence, although intervening sites may be omitted.

In the compounds of the present invention, FSHβ represents the FSHβ subunit from the appropriate species in essentially unaltered form except for the possible deletion, and/or insertion, and/or substitution of 1–5 amino acids wherein an substitution or insertion may be, but need not be conservative, in order to form variants. Thus, the FSHβ portion of the molecule, although minor variations are permitted, is essentially a constant feature.

The FSHβ subunit is optionally linked through linker$^1$ to the downstream portion of the molecule. The linker$^1$ may vary in the same manner as linker$^2$, as described below. However, linker$^1$ is preferably a complete CTP linker containing CG/β amino acids 112–118 to 145 with only minor variants—i.e., 1–5 amino acids substitutions, and/or insertions, and/or deletions included. Such alterations would preferably not affect the glycosylation sites.

The LHβ(1-X) portion of the molecule is more variable. The designation 1-X represents the amino acid sequence of LHβ included; X is 114–121. Thus, the LHβ subunit may comprise only the N terminal 114 amino acids of the 121 which occur in the native human hormone or, of course, the corresponding positions of an LHβ derived from a different species. Thus, the LHβ may include positions 1-114, 1-115, 1-116, up to 1-121. In addition, the LHβ subunit may contain 1–5 arbitrary amino acid substitutions, and/or insertions, and/or deletions, but may contain more substitutions when these are related to CGβ, as further described. Particularly preferred are substitution of amino acids of which are present in the corresponding positions in chorionic gonadotropin. Thus, an additional variable which permits alteration of the LH activity may be included by virtue of selected mutations which bridge the differences between LHβ and CGβ subunits. In general, LH in positions 1-121 is more hydrophobic than CG in the corresponding positions. It appears that intracellular activity is skewed in favor of CG; indeed, a preferred embodiment of the invention includes, in place of "LHβ-linker," various truncated (or un-truncated) forms of CGβ. Preferred embodiments of the invention include those wherein one or more of the amino acids present in the LHβ moiety is replaced by the corresponding amino acid in CGβ at that position.

There are 17 residues at positions 1-114 which are different in LH and CGβ. All of the amino acids at positions 115–121 differ. By systematically replacing LH amino acids with those of CGβ, the activity of the compound as a LH/CG receptor agonist can be altered. Thus, the specific replacements expand the compounds within the range of LH activities encompassed by the invention compounds.

The linker$^2$ downstream of the LHβ(1-X) is also optional. The linker is a sequence of amino acids, typically, 1–100 amino acids, preferably 1–75 amino acids, preferably 1–50, and more preferably 1–40. The amino acid sequence should be flexible and hydrophilic. Typical amino acids for inclusion in the linker include glypine, serine, and repeating gly/ser sequences are preferred. A particularly preferred embodiment is CTP', which is a partial or complete CTP unit.

The α subunit and its variants are as defined herein for variants in general.

Particularly preferred embodiments of the hormones of the invention include, shown N-C:

FSHβ-CTP-LHβ(1-114)-α;

FSHβ-CTP-LHβ(1-115)-α;

FSHβ-CTP-LHβ(1-116)-α;

FSHβ-CTP-LHβ(1-117)-α;

FSHβ-CTP-LHβ(1-118)-α;

FSHβ-CTP-LHβ(1-119)-α;

FSHβ-CTP-LHβ(1-120)-α;

FSHβ-CTP-LHβ(1-121)-α;

FSHβ-CTP-LHβ(1-114)CTP'-α;

FSHβ-CTP-LHβ(1-115)CTP'-α;

FSHβ-CTP-LHβ(1-116)CTP'-α;

FSHβ-CTP-LHβ(1-117)CTP'-α;

FSHβ-CTP-LHβ(1-119)CTP'-α;

FSHβ-CTP-LHβ(1-120)CTP'-α; and

FSHβ-CTP-LHβ(1-121)CTP'-α where CTP' represents a complete CTP.

Also preferred are the foregoing embodiments wherein the CTP' between the LHβ subunits and the α subunit is a partial CTP.

Also preferred are embodiments similar to those listed wherein one or more amino acids of the LHβ subunit residue are replaced by the corresponding amino acid from the CGβ subunit. Thus, amino acids in any of the relevant positions in the region 1-114 can be replaced, so that 1-17 such substitutions can be made; in addition, any number of the amino acids in positions 115-121 of LHβ subunit can be replaced by the corresponding amino acids in those positions in the CGβ subunit. In one particularly preferred embodiment, all of such replacements have been made and the CTP linker to the α subunit is simply that naturally occurring in the CGβ subunit. In addition, the CGβ subunit can be further extended by at least a portion of CTP. The following embodiments exemplify, for illustration purposes only, the types of substitutions that can be made wherein the LHβ subunit residue is "morphed" into a CGβ subunit. The illustrations are set forth with respect to the human hormones, but similar substitutions may occur with respect to the hormones from other animal species.

FSHβ-CTP-LH(1-114, H10R, M42T)-CTP'-α

FSHβ-CTP-LH(1-116, T8R, N71D, L115F, S116Q)-CTP'-α

FSHβ-CTP-LH(1-114, R2K, 115T, T53N, P83A)-CTP-α

FSHβ-CTP-LH(1-118, W8R, P51A, F82Y, G117D)-CTP'-α

FSHβ-CTP-CGβ-α

In the compounds set forth above, the standard one-letter amino acid code is used; the number indicates the position and the residue to the left is that of LH, that to the right is the residue from CGβ; thus, for example, "W8R" refers to an embodiment wherein the tryptophan residue of LH at position 8 is replaced by an arginine residue.

While for human use, the human forms of the α and β subunits are desirable, it should be noted that the corresponding forms in other vertebrates are useful in veterinary contexts. The FSH, TSH and LH subunits from bovine, ovine, equine, porcine, feline, canine, and other species are appropriate to indications affecting these species.

While not wishing to be bound by any theory, applicants believe that the LH activity of the molecule is enhanced by extending the C terminus of the LH component. Thus, it appears that the spectrum of activity ranges from compounds wherein LHβ is present as positions 1-114 and CTP is not included (having the lowest activity) to embodiments wherein the LHβ subunit is included in its entirety and further extended by CTP (to provide molecules of the greatest activity). The correlation is not, of course, perfect and will be influenced by any variations in the amino acid sequences of the components. Nevertheless, the foregoing provides some general guidance in constructing the range of activities desirable in the compounds of the invention; the LH agonist activity can generally be enhanced by extending the C-terminus sequence of the LHβ subunit portion of the molecule and LH agonist activity can be diminished by decreasing the length of this extension.

Other Modifications

The single-chain proteins of the invention may be further conjugated or derivatized in ways generally understood to modify amino acid sequences, such as phosphorylation, glycosylation (both N- and O- linked), deglycosylation of ordinarily glycosylated forms, acylation, modification of amino acid side chains (e.g., conversion of proline to hydroxyproline) and similar modifications analogous to those posttranslational events which have been found to occur generally.

The glycosylation status of the hormones of the invention is particularly important. The hormones may be prepared in nonglycosylated form either by producing them in prokaryotic hosts or by mutating the glycosylation sites normally present in the subunits and/or any CTP units that may be present. Both nonglycosylated versions and partially glycosylated versions of the hormones can be prepared by manipulating the glycosylation sites. Normally, glycosylated versions are, of course, also included within the scope of the invention.

As is generally known in the art, the single-chain proteins of the invention may also be coupled to labels, carriers, solid supports, and the like, depending on the desired application. The labeled forms may be used to track their metabolic fate; suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels permits localization of the relevant receptors since they can be used as targeting agents for such receptors.

The proteins of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of biofunctional linkers, can be employed.

Similar linking techniques, along with others, may be employed to couple the proteins of the invention to solid supports. When coupled, these proteins can then be used as affinity reagents for the separation of desired components with which specific reaction is exhibited. Thus, they are useful in the purification and isolation of the receptors with which the appropriate α subunit interacts.

Preparation Methods

Methods to construct the proteins of the invention are well known in the art. The most practical approach at present is to synthesize these materials recombinantly by, expression of the nucleotide sequence encoding the desired protein. A nucleic acid containing the nucleotide sequence encoding the single-chain forms, including variants, can be prepared from native sequences, or synthesized de novo or using combinations of these techniques. Techniques for site-directed mutagenesis, ligation of additional sequences, amplification such as by PCR, and construction of suitable expression systems are all, by now, well known in the art. Portions or all of the DNA encoding the, desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available compatible with a wide variety of hosts, including prokaryotic hosts such as E. coli or B. subtilis and eucaryotic hosts such as yeast, other fungi such as Aspergillus and Neurospora, plant cells, insect cells, mammalian cells such as CHO cells, avian cells, and the like.

The choice of host is particularly pertinent to posttranslational events, most particularly including glycosylation. The location of glycosylation is mostly controlled by the nature of the glycosylation sites within the molecule; however, the nature of the sugars occupying this site is also influenced by the nature of the host. Accordingly, a fine-tuning of the properties of the hormones of the invention can be achieved by proper choice of host.

A particularly preferred form of gene for the α subunit portion, whether the a subunit is modified or unmodified, is the "minigene" construction. As used herein, the α subunit "minigene" refers to the gene construction disclosed in Matzuk, M. M., et al., *Mol Endocrinol* (1988) 2:95–100, in the description of the construction of pM$^2$/CG α or pM$^{2/\alpha}$.

For recombinant production, modified host cells using expression systems are used and cultured to produce the desired protein. These terms are used herein as follows:

A "modified" recombinant host cell, i. e:, a cell "modified to contain" the recombinant expression systems of the invention, refers to a host cell which has been altered to contain this expression system by any convenient manner of introducing it, including transfection, viral infection, and so forth. "Modified cells" refers to cells containing this expression system whether the system is integrated into the chromosome or is extrachromosomal. The "modified cells" may either be stable with respect to inclusion of the expression system or the encoding sequence may be transiently expressed. In short, recombinant host cells "modified" with the expression system of the invention refers to cells which include this expression system as a result of their manipulation to include it, when they natively do not, regardless of the manner of effecting this incorporation.

"Expression system" refers to a nucleic acid molecule which includes a coding nucleotide sequence to be expressed and those accompanying control sequences necessary to effect the expression of the coding sequence. Typically, these controls include a promoter, termination regulating sequences, and, in some cases, an operator or other mechanism to regulate expression. The control sequences are, those which are designed to be functional in a particular target recombinant host cell and therefore the host cell must be chosen so as to be compatible with the control sequences in the constructed expression system.

If secretion of the protein produced is desired, an additional nucleotide sequence encoding a signal peptide is also included so as to produce the signal peptide operably linked to the desired single-chain hormone to produce the preprotein. During translation, the signal peptide is cleaved to release the mature single-chain hormone.

As used herein "cells," "cell cultures," and "cell lines" are used interchangeably without particular attention to nuances of meaning. Where the distinction between them is important, it will be clear from the context. Where any can be meant all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

All or a portion of the hormones of the invention may be synthesized directly using peptide synthesis techniques known in the art and synthesized portions may be ligated chemically or enzymatically.

Antibodies

The proteins of the invention may be used to generate antibodies specifically immunoreactive with these new compounds. These antibodies are useful in a variety of diagnostic and therapeutic applications.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the proteins of the invention. "Antibodies" include any fragment which retains the required immunospecificity, such as $F_{ab}$, $F_{ab'}$, $F_{(ab')2}$, $F_v$ and so forth. Thus, the antibodies may also be prepared using recombinant techniques, typically by isolating nucleotide sequences encoding at least the variable regions of monoclonal antibodies with the appropriate specificity and constructing appropriate expression systems. This approach permits any desired modification such as production of $F_v$ forms, chimeric forms, "humanized" forms and the like.

By "immunospecific for the proteins of the invention" is meant antibodies which specifically bind the referent compound of the invention, but not the heterodimers or any of the included subunits per se or any single-chain forms which include only a single β subunit, within the general parameters considered to determine affinity or nonaffinity. It is understood that specificity is a relative term, and an arbitrary limit could be chosen, such as a difference in specific binding of 100-fold or greater. Thus, an immunospecific antibody included within the invention is at least 100 times more reactive with the specified protein than with the corresponding heterodimers, prior art single-chain forms or separate subunits. Such antibodies can be obtained, for example, by screening for those that bind the invention compounds and discarding those that also bind the heterodimers, subunits or prior art single-chain forms set forth in WO95/22340, WO96/05224, and WO99/25849.

Formulation and Methods of Use

The proteins of the invention are formulated and administered using methods comparable to those known for the heterodimers corresponding to them. Thus, formulation and administration methods will vary according to the particular hormone or hormone combination used. However, the dosage level and frequency of administration may be altered as compared to the heterodimer, especially if CTP units are present in view of the extended biological half life due to its presence.

Formulations for proteins of the invention are those typical of protein or peptide drugs such as found in *Remington's Pharmaceutical Sciences*, latest edition, Mack Publishing Company, Easton, Pa. Generally, proteins are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches. Oral administration is also possible provided the formulation protects the peptides of the invention from degradation in the digestive system.

Optimization of dosage regimen and formulation is conducted as a routine matter and as generally performed in the art. These formulations can also be modified to include those suitable for veterinary use.

The compounds of the invention may be used in many ways, most evidently as substitutes for the heterodimeric forms of the hormones. Thus, like the heterodimers, the agonist forms of the single-chain hormones of the invention can be used in treatment of infertility, as aids in in vitro fertilization techniques, and other therapeutic methods associated with the native hormones. These techniques are applicable to humans as well as to other animals. The choice of the single-chain protein in terms of its species derivation will, of course, depend on the subject to which the method is applied.

The invention compounds are also useful as reagents in a manner similar to that employed with respect to the heterodimers.

In addition, the compounds of the invention may be used as diagnostic tools to detect the presence or absence of antibodies that bind to the native proteins to the extent such antibodies bind to the relevant portions of these single chain compounds in biological samples. They are also useful as control reagents in assay kits for assessing the levels of these hormones in various samples. Protocols for assessing levels of the hormones themselves or of antibodies raised against them are standard immunoassay protocols commonly known in the art. Various competitive and direct assay methods can be used involving a variety of labeling techniques including radio-isotope labeling, fluorescence labeling, enzyme labeling and the like.

The compounds of the invention are also useful in detecting and purifying receptors to which the native hormones bind. Thus, the compounds of the invention may be coupled to solid supports and used in affinity chromatographic preparation of receptors or antihormone antibodies. The resulting receptors are themselves useful in assessing hormone at for candidate drugs in screening tests for therapeutic and reagent candidates. Of course, account must be taken of the dual specificity of the β subunits since the β subunits are different.

Finally, the antibodies uniquely reactive with the compounds of the invention can be used as purification tools for isolation of these materials in their subsequent preparations. They can also be used to monitor levels of these compounds administered as drugs.

The following examples are intended to illustrate but not to limit the invention.

EXAMPLE 1

Preparation of Invention Compounds

Expression vectors were prepared for production of the proteins and their secretion from Chinese hamster ovary (CHO) cells. The compounds that were prepared and tested are as follows:

FSHβ-CTP-LHβ(1-114)-α;

FSHβ-CTP-LHβ(1-121)-α; and

FSHβ-CTP-LHβ(1-114)-CTP-α.

Also constructed is an expression vector for the production of:

FSHβ-CTP-LHβ(1-121)-CTP-α.

EXAMPLE 2

Binding of the LH or FSH Receptor

The compounds of Example 1 were tested for their ability to compete with I-125 labeled hCG or FSH heterodimers as appropriate. The procedures for assay are those set forth in Kanda, M., et al., *Mol Endocrinol* (1999) 13:1873–1881, cited above and incorporated herein by reference.

Briefly, for assessing binding to the CG/LH receptor, CHO cells expressing human LH receptor ($4 \times 10^5$/tube) were incubated with one ng labeled CG in competition with increasing concentrations of unlabeled CG as a standard or with increasing amounts of the samples to be tested, at 22° C. for 18 hours. The decrease in label in the presence of sample measures the binding ability in the sample. The results are shown in FIG. 1.

As shown, none of the constructs shows activity comparable to that of the CG heterodimer (solid diamonds). However, the construct FSHβ-CTP-LHβ(1-114)-CTP-α (solid circles and single cross line) provides an $EC_{50}$ approximately 10 fold more than the native hormone. The construct FSHβ-CTP-LH(1-121)-α (solid squares and solid triangles) shows a still somewhat greater $EC_{50}$. It does not appear that the construct FSHβ-CTP-LHβ(1-114)-α exhibits much activity at all in this assay (open circles and crosses).

Figure 2:
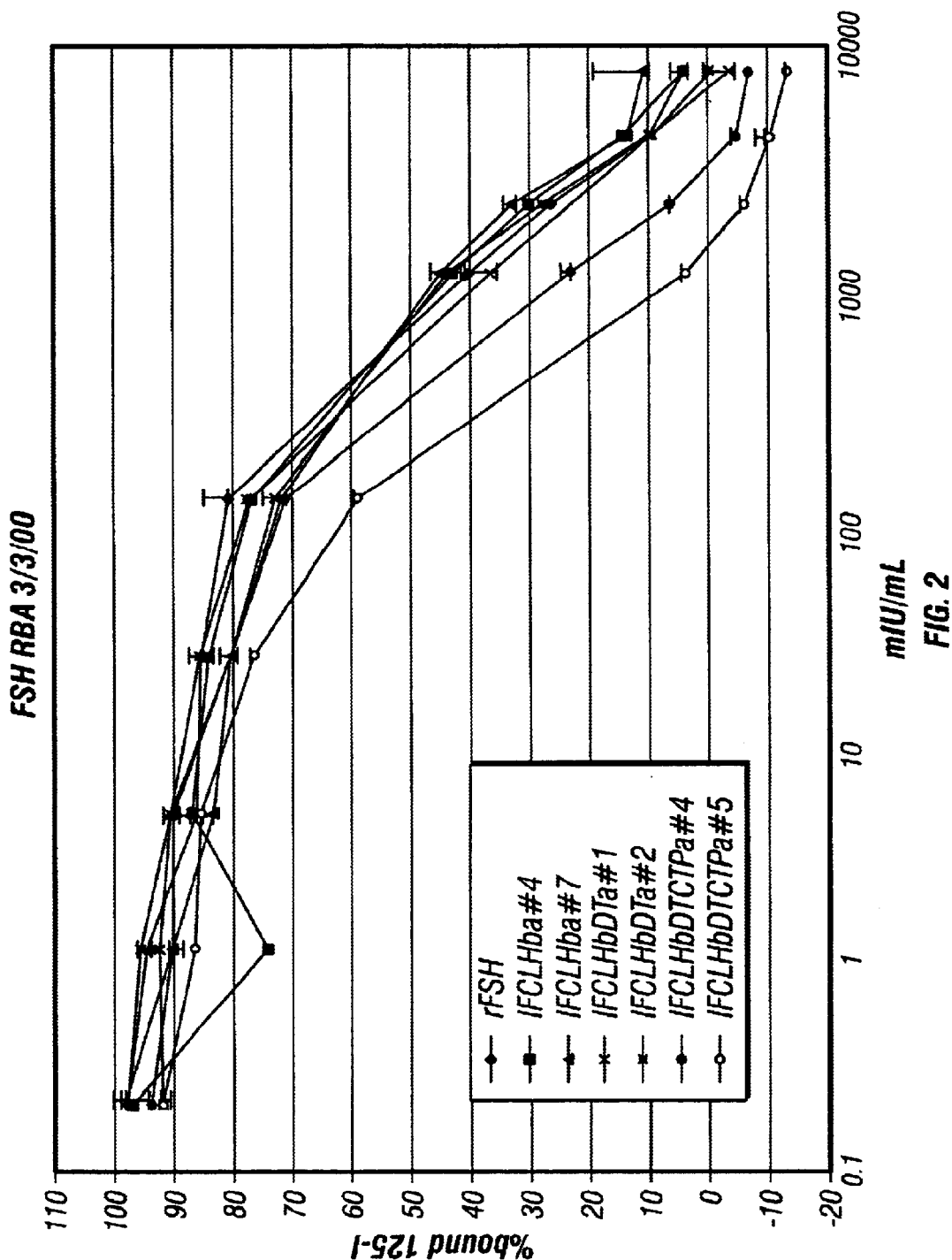
FIG. 2 shows the binding of various compounds of the invention to the FSH receptor in competition with FSH.

In a comparable essay testing ability of the compounds to bind the FSH receptor displayed on CHO cells in competition with I-125 labeled FSH, in protocol otherwise identical to that set forth above, all of the compounds showed roughly comparable FSH receptor binding activity. See FIG. 2. The construct FSHβ-CTP-LHβ(1-114)-CTP-α (solid and open circles) appears slightly more effective than the remaining molecules tested, including recombinant FSH heterodimer.

EXAMPLE 3

Agonist Activity With Respect to LH

Some of the compounds of the invention were tested for their ability to stimulate cyclic AMP production in CHO cells that display the CG/LH receptor or the FSH receptor. The procedure was that of Kanda, et al., (1999) cited above. Briefly, the total extracellular and intracellular amount of cAMP was determined using the Adenyl Cyclase Activation Flash Plate Kit (NEN Life Science Products, Boston Mass.) as per the manufacturer's instructions. CHO cells ($5 \times 10^4$ cells per well) expressing either the LH/CG or FSH receptor were incubated with ligand for 2 hours at room temperature. cAMP labeled with I-125 was added and the cells were incubated for an additional 16–18 hours at room temperature. The flash plates were read in a Packard Top gamma counter and each experiment was performed 2–3 times. The cAMP content was expressed in pmol/ml.

Figure 3A:
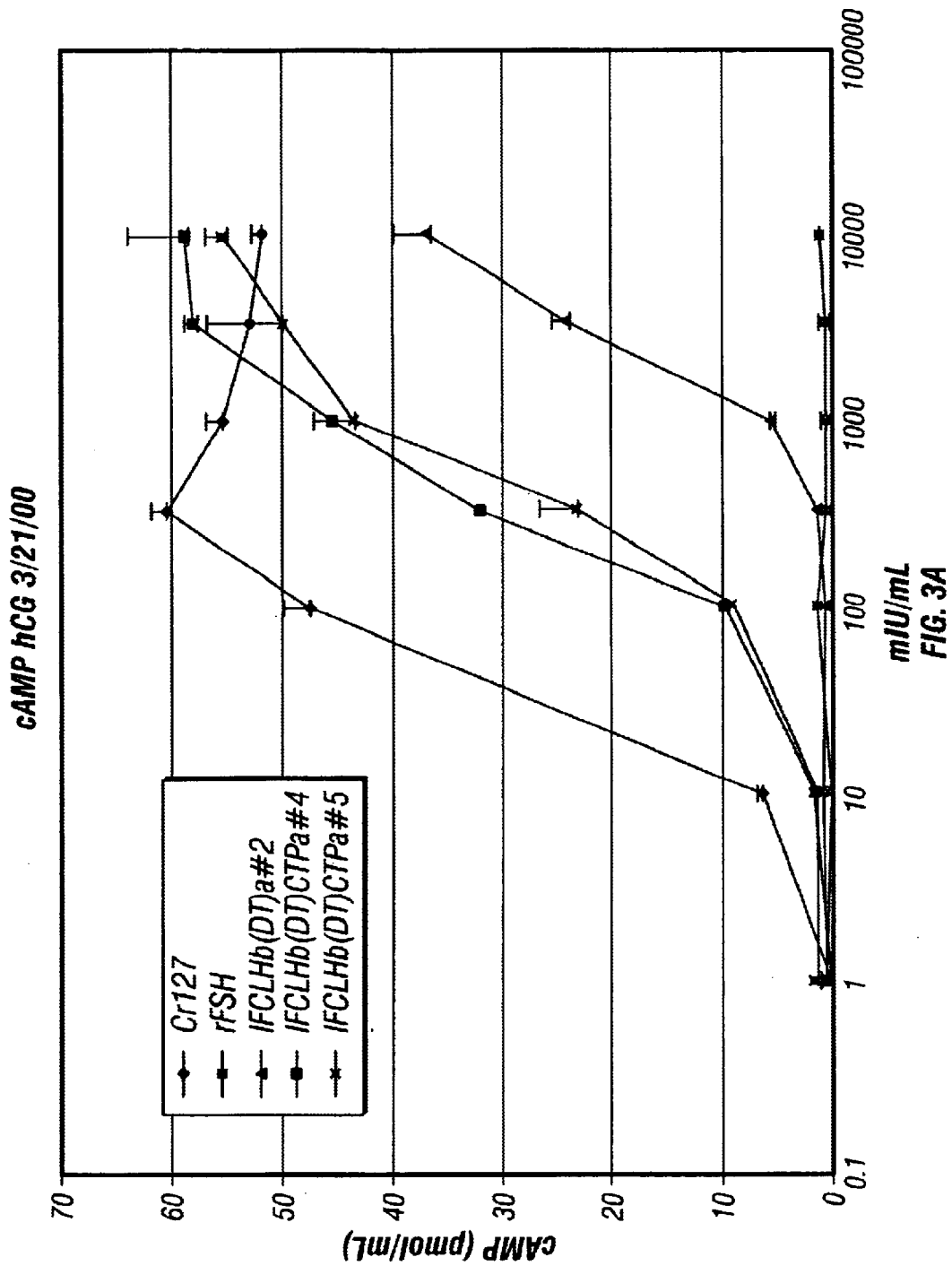
FIGS. 3A and 3B show the ability of various compounds of the invention to induce the production of cyclic AMP in CHO cells modified to produce the LH/CG receptor.
Figure 3B:
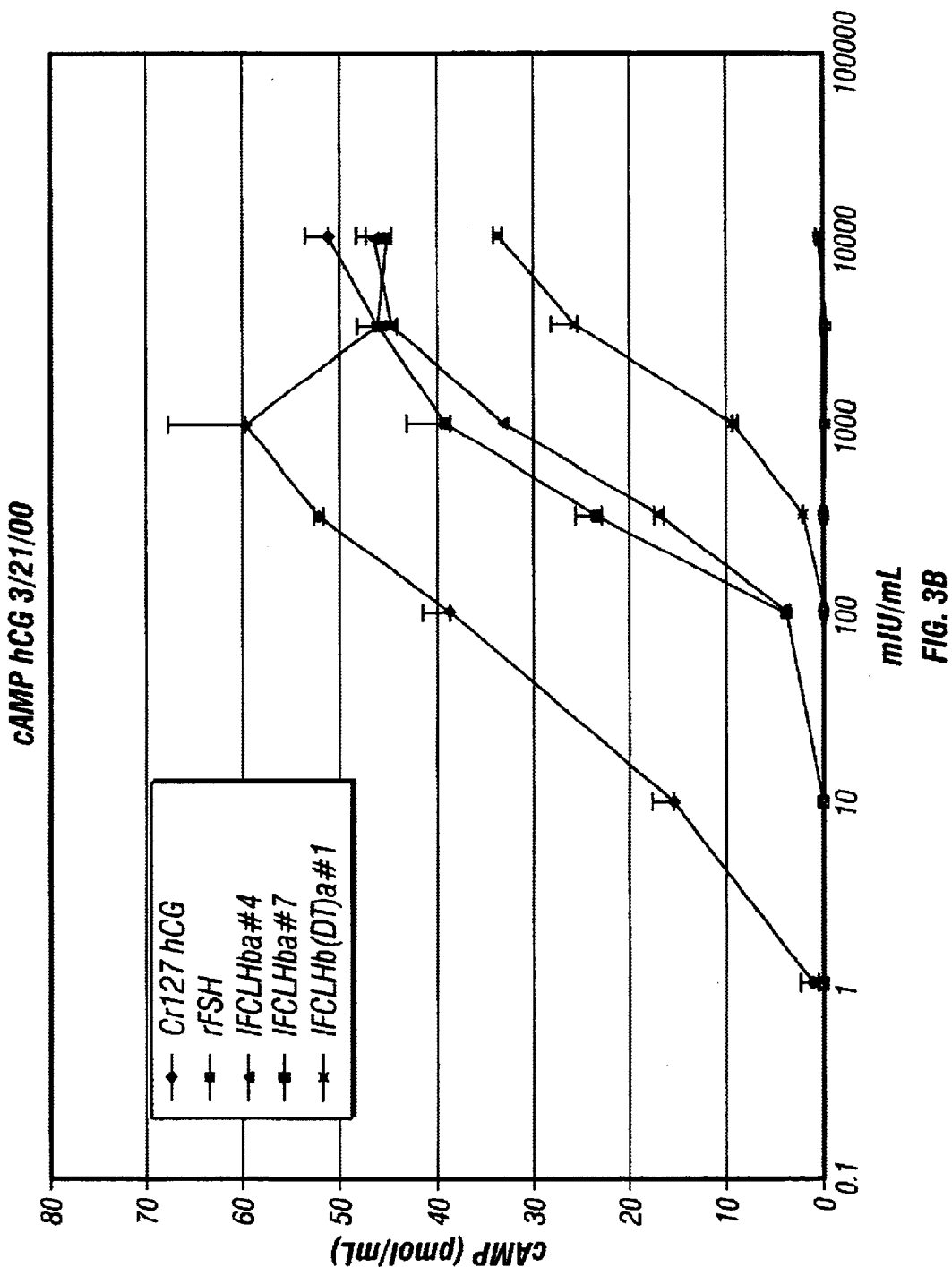

FIGS. 3A and 3B show the results for CG/LH agonist activity. As indicated the construct FSHβ-CTP-LHβ(1-114) CTP-α (solid squares or crosses) was somewhat less effective than heterodimeric recombinant hCG (CR127, solid diamonds) in this assay; however, the compound was much more effective than the construct FSHβ-CTP-LHβ(1-114)-α (solid triangles). The control FSH, as expected does not provide a response in these cells.

Figure 4A:
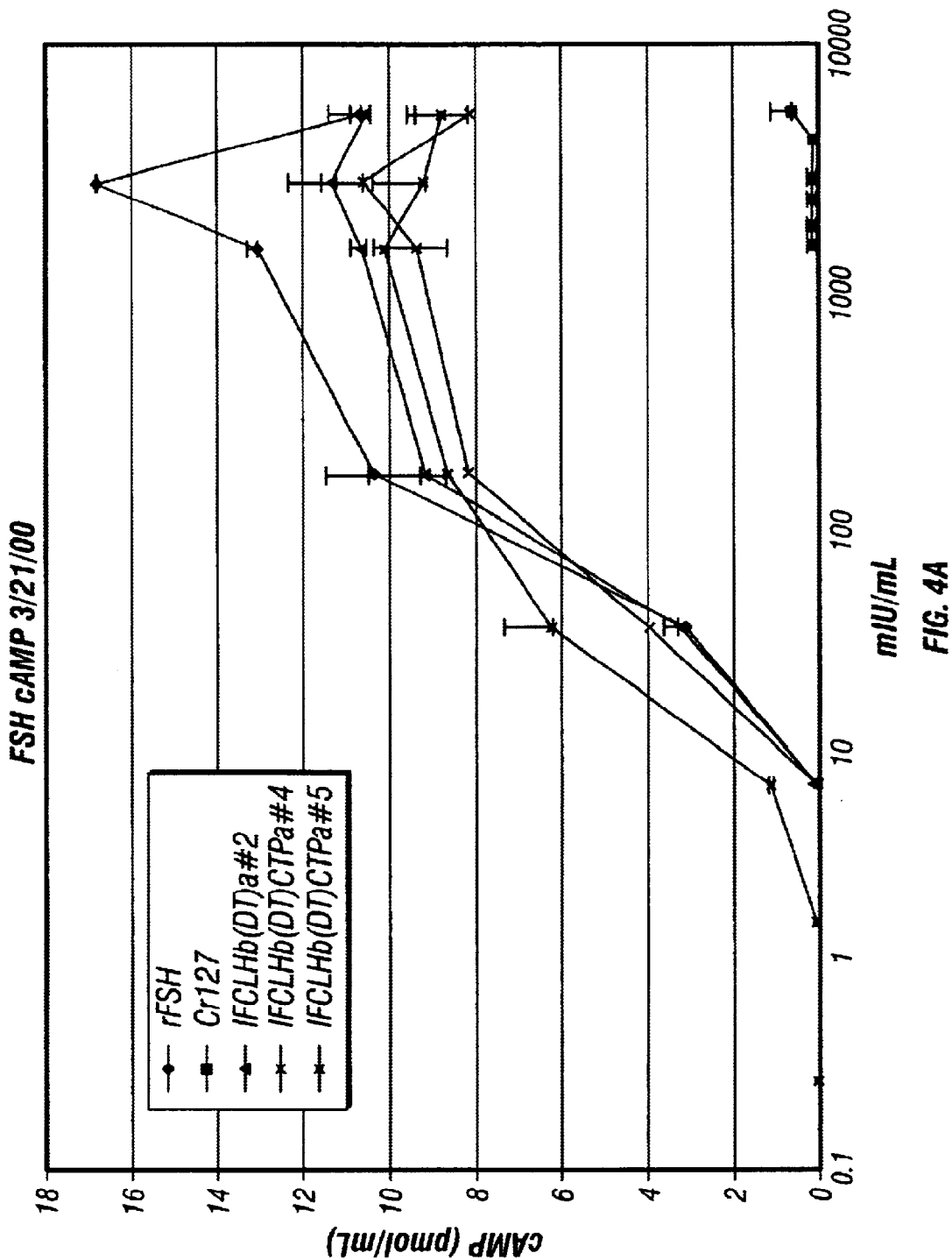
FIGS. 4A and 4B show the ability of various compounds of the invention to induce the production of cyclic AMP in CHO cells modified to produce the FSH receptor.
Figure 4B:
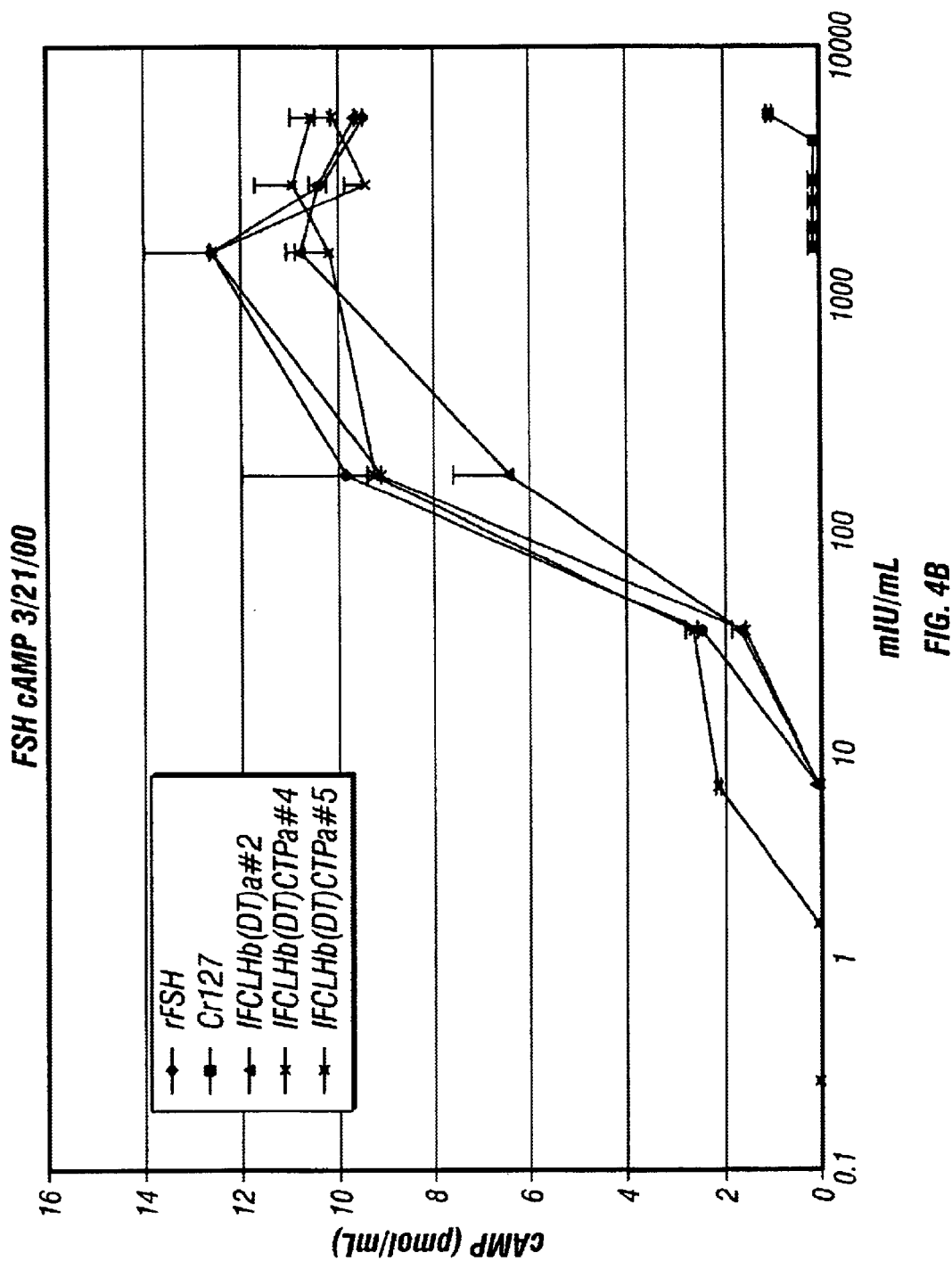

FIGS. 4A and 4B show the results for FSH agonist activity. As expected, hCG (solid squares) is not able to generate cAMP in cells displaying the FSH receptor; however, FSH heterodimer (solid diamonds) does so. Both compounds of the invention tested, FSHβ-CTP-LHβ(1-114)-α (solid triangles) and FSHβ-CTP-LHβ(1-114) CTP-α (crosses) provided responses comparable to those of heierodimeric recombinant FSH.

What is claimed is:

1. A glycosylated or nonglycosylated protein having FSH activity and LH activity, of the formula

FSHβ-(linker$^1$)$_n{}^1$-LHβ(1-X)-(linker$^2$)$_n{}^2$-α wherein FSHβ is a vertebrate follicle stimulating hormone β subunit or a variant thereof;

LHβ(1-X) refers to a β subunit of a vertebrate luteinizing hormone containing positions 1-X where X is an integer of 114–121 or a variant thereof;

each "linker" is a hydrophilic, flexible amino acid sequence containing 1–100 amino acid residues;

each n is a 0 or 1; and

α is the α subunit of a vertebrate glycoprotein hormone or a variant thereof.

2. The protein of claim 1 wherein n$^1$ is 1.

3. The protein of claim 2 wherein linker$^1$ is a complete or partial CTP comprising at least one glycosylation site or a variant thereof, wherein CTP refers to the amino acid sequence at positions 112–118 to 145 of human chorionic gonadotropin β subunit.

4. The protein of claim 1 wherein n$^2$ is 1.

5. The protein of claim 4 wherein linker$^2$ is a complete or partial CTP comprising at least one glycosylation site or is a variant thereof.

6. The protein of claim 1 wherein FSHβ is human FSHβ, LHβ is human LHβ and α is the human alpha subunit.

7. The protein of claim 1 which is FSHβ-CTP-LH(1-121)-CTP-α or

FSHβ-CTP-LHβ(1-114)-CTP-α, or

FSHβ-CTP-LHβ(1-121)-α, or

FSHβ-CTP-LHβ(1-114)-α or

FSHβ-CTP-CGβ-α.

8. A pharmaceutical composition which comprises the protein of claim 1 in admixture with a suitable pharmaceutical excipient.

9. The protein of claim 1 coupled to a solid support.

10. A DNA or RNA molecule which comprises a nucleotide sequence encoding the protein of claim 1.

11. An expression system for production of an agonist of FSH and LH which expression system comprises a first nucleotide sequence encoding the protein of claim 1 operably linked to control sequences for effecting the expression of said first nucleotide sequence.

12. The expression system of claim 11 which further contains a second nucleotide sequence encoding a signal peptide operably linked to the protein encoded by said first nucleotide sequence.

13. A host cell modified to contain the expression system of claim 12.

14. A method to produce a single-chain protein wish is an agonist of FSH and LH which method comprises culturing the cells of claim 13 under conditions wherein said protein is produced; and recovering said protein from the culture.

15. A host cell modified to contain the expression system of claim 11.

16. A method to produce a single-chain protein which is an agonist of FSH and LH which method comprises culturing the cells of claim 15 under conditions wherein said protein is produced; and recovering said protein from the culture.

* * * * *